United States Patent [19]

Pierce et al.

[11] Patent Number: 4,662,357

[45] Date of Patent: May 5, 1987

[54] INFLATABLE SURGICAL IMPLANT WITH VARIABLE INFLATION POSITION

[75] Inventors: David L. Pierce, Bay City; Judy L. Wisniewski, Pontiac, both of Mich.

[73] Assignee: Dow Corning Corporation, Midland, Mich.

[21] Appl. No.: 820,343

[22] Filed: Jan. 21, 1986

[51] Int. Cl.$^4$ .................... A61B 19/00; A61F 6/00
[52] U.S. Cl. ......................... 128/1 R; 623/8; 623/11
[58] Field of Search ............ 604/93, 96, 175, 283, 604/248, 326, 332, 905, 8, 11; 128/1 R; 273/65 D; 137/223; 277/27, 53, 135

[56] References Cited

U.S. PATENT DOCUMENTS

| | | | |
|---|---|---|---|
| 2,073,766 | 3/1937 | Suzuki | 273/65 D |
| 3,063,462 | 11/1962 | Potash | 137/223 |
| 3,170,482 | 2/1965 | Wicoff | 277/135 |
| 3,343,542 | 9/1967 | Ericson | 604/325 |
| 3,905,387 | 9/1975 | Grant | 137/223 |
| 4,190,040 | 2/1980 | Schulte | 128/1 R |
| 4,235,446 | 11/1980 | Verhey | 277/135 |
| 4,280,498 | 7/1981 | Jensen | 604/248 |
| 4,320,776 | 3/1982 | Yang | 273/65 D |
| 4,341,382 | 7/1982 | Arnold | 273/65 D |
| 4,543,088 | 9/1985 | Bootman et al. | 604/93 |

Primary Examiner—Stephen C. Pellegrino
Attorney, Agent, or Firm—Richard E. Rakoczy

[57] ABSTRACT

An inflatable surgical implant having a remotely located inflation button also designed for implantation and adopted to be pierced by a hypodermic needle. A fluid conduit connector in the wall of the implant for fluid communication with the inflation button has a center element which is rotatable in a cup-shaped elastomeric fixed element. A flange in the fixed element cooperating with a groove in rotatable element holds the rotatable element in place. The fixed element is made of elastomeric material such as silicone rubber which is forced by internal pressure into fluid tight relationship with the rotating element. Silicone fluid is optionally placed between the two elements to further effect positive sealing. As an alternate, an integral inflation button may be built into the rotatable element to allow the surgeon a choice of inflation sites.

12 Claims, 4 Drawing Figures

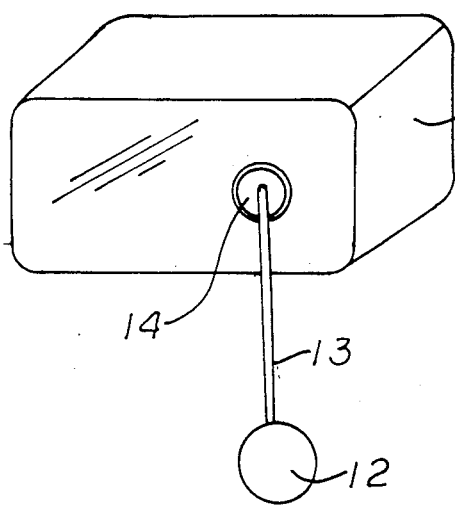
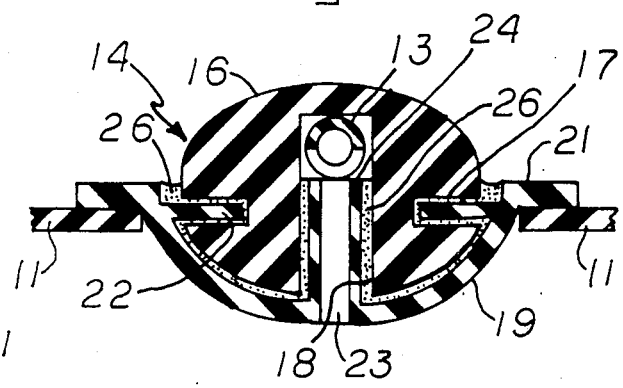
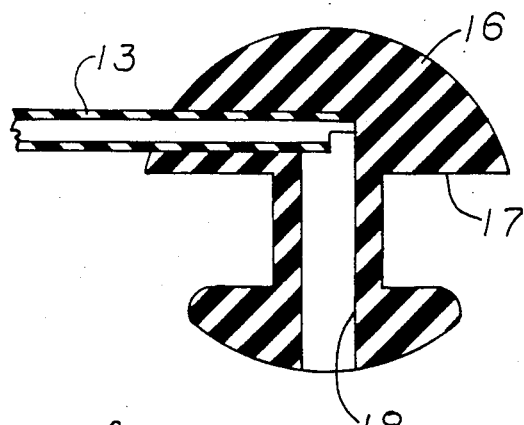
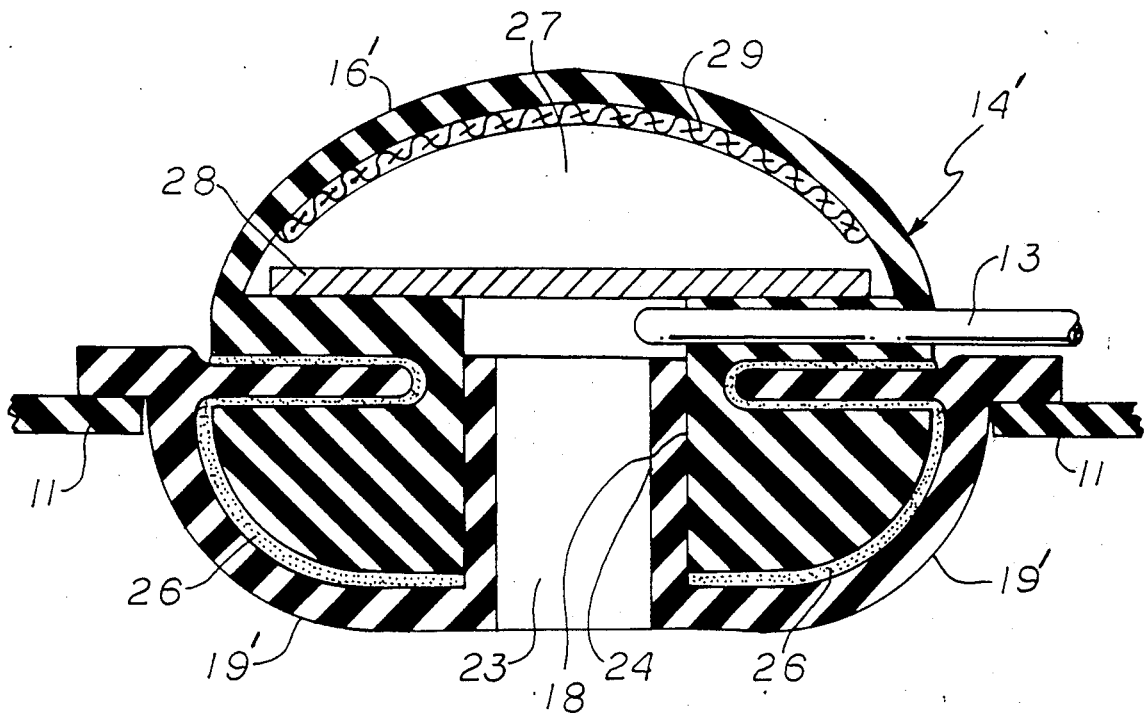

INFLATABLE SURGICAL IMPLANT WITH VARIABLE INFLATION POSITION

BACKGROUND OF THE INVENTION

This invention relates to improvements in surgically implantable inflatable devices.

Tissue expansion devices of the general type illustrated in Radovan et al. U.S. Pat. No. 4,217,889 are finding substantial use in reconstructive surgery. Such devices generally comprise an inflatable body having a remotely located inflation button or valve connected to the inflatable body by means of an elongated conduit. The body is placed subcutaneously in the area in which the tissue is to be expanded and the valve and connecting conduit are implanted to allow gradual introduction of fluid into the device by injection into the inflation valve at a site remote from the body itself. After gradual inflation at intervals of weeks or even months the tissue has been expanded to the point where a permanent prosthesis can be inserted or a skin flap formed as desired and the expander is deflated and surgically removed. It is believed by some surgeons that the use of a remote location for the inflation valve minimizes risk of infection in the vicinity of the implant which might occur at any time during the period of injection of further fluid. Similar implants in which the inflation valve is located on the wall of the inflatable body itself and which, of course, lack the remote valve feature, are also currently in use and are preferred by some surgeons. Similarly, inflatable permanent prostheses are sometimes implanted and filled and/or reduced after implantation.

Particularly when asymmetrically shaped implantable devices are used the surgeon sometimes finds that the direction which the inflation conduit and valve extend away from the unit do not correspond to the preferred direction for placement of the conduit and valve. Although the conduit is typically flexible the surgeon must guard against kinking it in changing direction and often would prefer to have a straight rather than curved conduit configuration for implanting. For the manufacturer and the hospital or clinic this may mean that a substantial number of devices of various configurations need to be manufactured and stocked to provide implants with and without remote valves and with remote valves extending from the inflatable portion of the device on conduits protruding at different angles.

SUMMARY OF PRESENT INVENTION

It is therefore an object of the present invention to provide an improved surgically implantable inflatable device which is more versatile than those presently available in order to provide more convenience for the surgeon and minimize need for manufacturing and stocking various configurations.

In accordance with the present invention there is provided a surgically implantable inflatable device in which the inflation conduit direction can be readily changed relative to the inflatable body. This is accomplished by provision of a soft elastomeric self sealing rotatable connection between the inflatable body and the inflation conduit. Further, there is provided an embodiment in which the rotatable connector can alternatively be used as an integral injection valve for inflation of the inflatable portion of the device. The device in either case provides assured sealing from application of either internal or external pressures to prevent fluid leakage.

Other objects and attendant advantages of the invention will become apparent to those skilled in the art from a consideration of the following detailed description when read in connection with the accompanying drawings.

BRIEF DESCRIPTION OF THE DRAWINGS

In the drawings:

FIG. 1 is a view in perspective of a surgically implantable tissue expander incorporating the present invention;

FIG. 2 is a vertical cross-sectional view taken through the center of the conduit connector incorporated in the embodiment shown in FIG. 1;

FIG. 3 is a vertical cross-sectional view of the rotatable element of the conduit connector shown in FIG. 2 taken through the center thereof and at right angles to the cross section shown in FIG. 2; and FIG. 4 is a vertical cross-sectional view similar to FIG. 2 of an alternative embodiment of the conduit connector which also includes means for allowing introduction of fluid directly into the connector.

DESCRIPTION OF PREFERRED EMBODIMENTS

Referring now to the drawings wherein like reference characters designate like or corresponding parts throughout the figures thereof there is shown in FIG. 1 a surgically implantable tissue expander having a flexible inflatable body 11. An injection button 12 is connected via a tubular fluid conduit 13 to a connector 14 mounted on the inflatable body 11. The injection button 12 may be of any conventional design suitable for implantation beneath the skin of a patient and designed to be pierced by a hypodermic needle for injection or removal of inflating fluid.

As may be seen more clearly from FIGS. 2 and 3 the connector 14 includes a rotatable element 16 having a circular cross-section in planes substantially parallel to the plane of the wall of the inflatable body 11 in the area adjacent the connector and having a circumferential groove 17 in its exterior surface. The fluid conduit 13 extends into the rotatable element 16 and is sealingly mounted therein in fluid communication with an opening 18 which extends axially upward from the bottom of the rotatable element.

The connector 14 further includes a substantially cup shaped fixed element 19 having an outwardly extending flange 21 which is affixed to the wall of the inflatable body 11 in sealing relationship therewith. The fixed element 19 further includes an inwardly extending circular flange 22 around its inner surface mating with the groove 17 in the rotatable element 14 which is retained thereby. The fixed element 19 has an opening 23 at the bottom thereof corresponding to the fluid conduit opening 18 in the rotatable element 14 in order to allow fluid communication between the interior of the rotatable element 14 and the interior of the inflatable body 11.

The fixed element 19 may further include a central tubular upward extension 24 surrounding the opening 23 to provide increased sealing area between the rotatable element 14 and the fixed element 19. If desired, a layer 26 of viscous material such as high viscosity silicone fluid may be interposed between the fixed and rotatable elements to provide lubrication and also to insure better sealing against leakage of inflation fluid. By molding the fixed element from relatively soft elastomeric material such as silicone rubber the device becomes self sealing because as fluid pressure is created inside the inflatable body pressure is exerted on the lower portion of the cup shaped fixed element 19 forcing it into tighter engagement with the lower portions of the rotatable element 14. Yet, prior to inflation the surgeon can easily change the direction in which the fluid conduit extends from the inflatable body by rotation of the connector.

The embodiment shown in FIG. 4 offers the surgeon a further choice between remote and integral injection sites. As shown, the fixed member 19' attached to the inflatable body 11 is substantially the same as the body 19 shown in FIGS. 2 and 3. As in the previously described embodiment there is shown a layer of viscous silicone fluid 26 interposed between the fixed element 19' and a rotatable element 16'. The rotatable element 16' differs from the previously described embodiment in that an injection button is in effect built into the element by making the rotatable element of soft material such as silicone elastomer and by providing in the top portion thereof a hollow injection chamber 27 having a needle stop 28 at or near its lower extremity. The needle stop may be of sintered or metallic material as is conventional in injection buttons presently commercially available, and is designed to prevent the hypodermic injection needle from penetrating beyond the hollow designed for receiving fluid. If desired, a layer 29 of soft sealing material may be incorporated inside the top wall of the hollow 27 to insure resealing as the injection needle is withdrawn. The hollow 27 is in fluid communication with the central opening 18 and thereby with the interior of the inflatable body 11. The fluid conduit 13 preferably is provided with a tubing connector so that the remote injection button 12 may be disconnected and the conduit 13 closed if the surgeon wishes to only utilize the integral injection valve formed in the rotatable element.

Other variations and modifications of the invention will become apparent to those skilled in the art from a reading of the above description of preferred embodiments of the invention. Accordingly it is to be understood that within the scope of the appended claims the invention may be practiced otherwise than as specifically described.

That which is claimed is:

1. In a flexible inflatable body having a fluid conduit connected therewith the improvement which comprises
   a fluid conduit connector mounted in the wall of the inflatable body and having a rotatable element;
   said rotatable element having a circular cross-section in planes substantially parallel to the plane of the wall of the inflatable body in the area adjacent the connector and having a circumferential groove in the exterior surface of the element,
   said rotatable element having an integral fluid conduit fixation opening above the circumferential groove and,
   said rotatable element having a fluid conduit opening for fluid communication between the fluid conduit fixation opening and the interior of the inflatable body and
   said connector further comprising a substantially cupshaped fixed element of elastomeric material sealingly mounted to the wall of the inflatable body, said fixed element having a circular flange around its inner surface mating with the groove in the rotatable element to retain the rotatable element within the fixed element, and having an opening through the bottom portion thereof corresponding to the fluid conduit opening in the rotatable element to allow fluid flow between the rotatable element and the interior of the inflatable body,
   whereby the location of the fluid conduit fixation opening enables the fluid conduit to extend in various directions relative to the inflatable body with rotation of the rotatable element, and
   whereby fluid pressure urges the bottom of the elastomeric fixed element and the flange on the interior surface thereof into sealing engagement with the rotatable element to prevent fluid leakage past the rotatable element.

2. The invention as defined in claim 1 and further including a layer of viscous material between the fixed and rotating elements to provide lubrication for rotation of the rotatable element and fixed element and enhancement of sealing between the two elements.

3. The invention as defined in claim 2 wherein the viscous material is a silicone fluid.

4. The invention as defined in claim 3 wherein the fixed element is a silicone elastomer.

5. The invention as defined in claim 4 wherein the rotatable element is a silicone elastomer.

6. The invention as defined in claim 5 wherein the device is a surgically implantable tissue expander.

7. The invention as defined in claim 1 wherein the fixed element includes a circular hollow conduit extending axially into the rotatable element to provide further sealing surfaces between the two bodies.

8. The invention as defined in claim 1 wherein the rotatable element is a silicone elastomer and further comprises a hollow fluid injection chamber under the surface thereof and in fluid communication with the fluid conduit opening through the connector and a needle stop of rigid material positioned at the bottom of the fluid injection chamber whereby the inflatable body may be inflated by inserting a hypodermic needle into the injection chamber through the top of the rotatable element.

9. The invention as defined in claim 8 and further including a layer of viscous sealing material on top of the injection chamber to aid in sealing as the hypodermic needle is withdrawn.

10. The invention as defined in claim 9 wherein the device is a surgically implantable tissue expander.

11. The invention as defined in claim 1 wherein the fixation opening is positioned so that near the connector the fluid conduit extends generally parallel to the plane of the wall of the inflatable body in the area adjacent the connector.

12. The invention as defined in claim 11 wherein the device is a surgically implantable tissue expander.

* * * * *